(12) United States Patent
Mohanty et al.

(10) Patent No.: US 8,841,119 B2
(45) Date of Patent: Sep. 23, 2014

(54) SENSOR FOR FAST DETECTION OF *E-COLI*

(75) Inventors: Pravansu S. Mohanty, Canton, MI (US); Ramesh K. Guduru, Canton, MI (US)

(73) Assignee: Mridangam Research Intellectual Property Trust, Canton, MI (US)

(*) Notice: Subject to any disclaimer, the term of this patent is extended or adjusted under 35 U.S.C. 154(b) by 167 days.

(21) Appl. No.: 13/187,587

(22) Filed: Jul. 21, 2011

(65) Prior Publication Data

US 2012/0021502 A1    Jan. 26, 2012

Related U.S. Application Data

(60) Provisional application No. 61/366,638, filed on Jul. 22, 2010.

(51) Int. Cl.
  *C12M 1/34* (2006.01)
  *G01N 21/76* (2006.01)
  *G01N 33/543* (2006.01)

(52) U.S. Cl.
  CPC .......... *G01N 21/76* (2013.01); *G01N 33/54373* (2013.01); *Y10S 436/805* (2013.01)
  USPC .......... 435/288.7; 385/12; 385/129; 385/130; 422/82.11; 435/7.37; 436/164; 436/524; 436/805

(58) Field of Classification Search
  None
  See application file for complete search history.

(56) References Cited

U.S. PATENT DOCUMENTS 4,882,288 A * 11/1989 North et al. .................. 436/525
5,310,686 A * 5/1994 Sawyers et al. ............... 436/518
2009/0219509 A1   9/2009 Nomura

OTHER PUBLICATIONS

Mathew et al., Porous silicon-based biosensor for pathogen detection, Biosensors and Bioelectronics, 20, 1656-1661(2005).*
International Search Report and Written Opinion dated Feb. 27, 2012 related to PCT/US2011/045031.

* cited by examiner

*Primary Examiner* — Chris L Chin
(74) *Attorney, Agent, or Firm* — Gifford, Krass, Sprinkle, Anderson & Citkowski, P.C.

(57) ABSTRACT

A method of fabricating biochip sensor comprising providing a precursor; depositing the precursor on a substrate to form a coating; and rapid melting/quenching treatment of the coating with an energy source to form micro/nanotextured surface with enhanced reflectance for fast chemiluminescence response of *E-Coli* bacteria.

10 Claims, 5 Drawing Sheets

SENSOR FOR FAST DETECTION OF E-COLI

CROSS-REFERENCE TO RELATED APPLICATIONS

This application claims the benefit of U.S. Provisional Patent Application No. 61/366,638, filed on Jul. 22, 2010. The entire disclosures of the above application are incorporated herein by reference.

FIELD OF THE INVENTION

The present disclosure relates to detection of *E-Coli* bacteria, and, more particularly, to a micro/nanoscale textured sensor for rapid chemiluminescence response.

BACKGROUND OF THE INVENTION

This section provides background information related to the present disclosure which is not necessarily prior art.

Among different types of food, water and other edible contaminations, the bacterial contamination is more commonly observed. The survival and growth of bacteria are always dependent on suitable ambient temperature, atmospheric conditions, moisture and the nutrients provided.

*E-Coli* is a very commonly observed bacteria in the food items such as peanut butter and spinach, etc., and consumption of *E-Coli* can lead to different types of health disorders, for example diarrhea.

Detection of *E-Coli* through usual standard biochemical testing procedures requires longer times (e.g.: 8 to 48 hrs) [Reference 1].

A fast sensor that can reliably detect the *E-Coli* in food, water and other media would avoid many health hazards in a short notice.

A simple and quick way to sensing *E-Coli* bacteria is through enzymatic chemiluminescence procedures. For example, the enzyme β-Galactosidase released by *E-Coli* as a part of its metabolic process can be a very useful biomarker.

The chemiluminescent substrate for β-Galactosidase is phenyl galactose-substituted dioxetane [References 2 and 3].

The Lumi Gal® 530, a commercial formulation of 4-methoxy-4-(3-b-D-galactosidephenyl)spiro[1,2-dioxetane-3,2'-adamantane] can also be a best substitute for the detection and quantification of β-Galactosidase activity [Reference 4].

The chemical reaction between the enzyme β-Galactosidase and dioxetane substrate results in the emission of a light wavelength around 530 nm and thus emitted light could be detected by a photodetector or luminometer to determine the presence of *E-Coli*.

Biosensors employing above discussed biomarker and assay have enabled rapid detection of *E-Coli* [Reference 2].

The efficacy and response time of such biosensors are highly dependent on the surface textures of the sensor; micro/nanostructured surfaces with high reflectance are desired.

In recent years, many studies have been performed on the surface texture of silicon wafer. The purpose is to produce a micro/nanostructure on the surface of silicon wafer, to increase the surface area considerably, and thus enhance the physiochemical process.

However, when the surface of the silicon wafer has a sub-wavelength structure that is smaller than the wavelength of the emitted light, a strong absorption effect can be produced.

Referring to FIG. 1, the reflectance of the surface is severely diminished with increased pore depth as exemplified in FIG. 2. Therefore, control of the depth, size and separation between these structures is critical for the efficacy of the sensor.

The pores on the silicon surface can be produced in KOH or NaOH etchant. Although such an alkaline etching technique is simple and low cost, it has drawbacks of being time consuming, requires heating and yields poor uniformity. The etching solution must be mechanically agitated for better uniformity of the textured structure on silicon surface. Besides, the presence of alkali metal ions in KOH or NaOH etchant is incompatible with bacteria proliferation, and may be detrimental to the efficacy of the sensor.

SUMMARY OF THE INVENTION

This section provides a general summary of the disclosure, and is not a comprehensive disclosure of its full scope or all of its features.

A micro/nanoscale textured sensor assembly for fast detection *E-Coli* bacteria is disclosed. The sensor assembly comprises a support substrate and a coating with geometrical characteristics to enhance chemiluminescence response.

Further, a method to achieve such ultrafine textured coating is also disclosed. The method comprises an appropriate material (e.g., silicon) being deposited using a deposition technique on a substrate and simultaneously/subsequently treated to achieve the desired topology that enhances the chemiluminescence response.

The deposition technique can be a plasma or similar technology and can employ a solid or gaseous precursor material.

The surface texturing technique can employ a laser, an electron beam, a plasma beam or any other intense heat source.

Thus prepared biochip is functionalized using a "Biomarker substrate mixture". An example of the Biomarker substrate mixture is Lumi Gal° 530 and a polymyxin-B-sulfate solution, which is also referred sometimes as "Substrate Mixture" in this whole document. Functionalization of the biochip is done with the above mentioned "biomarker substrate mixture", for an overnight period in a refrigerator at 4-6° C. in order to facilitate the marker diffusion and adsorption into the sensor surface. Thus functionalized biochip is ready for detection of *E-Coli*.

Further applicability will become apparent from the description provided herein. The description and specific examples in this summary are intended for purposes of illustration only and are not intended to limit the scope of the present disclosure.

BRIEF DESCRIPTION OF THE DRAWINGS

The figures and drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION OF THE PRESENT INVENTION

Figure 1:
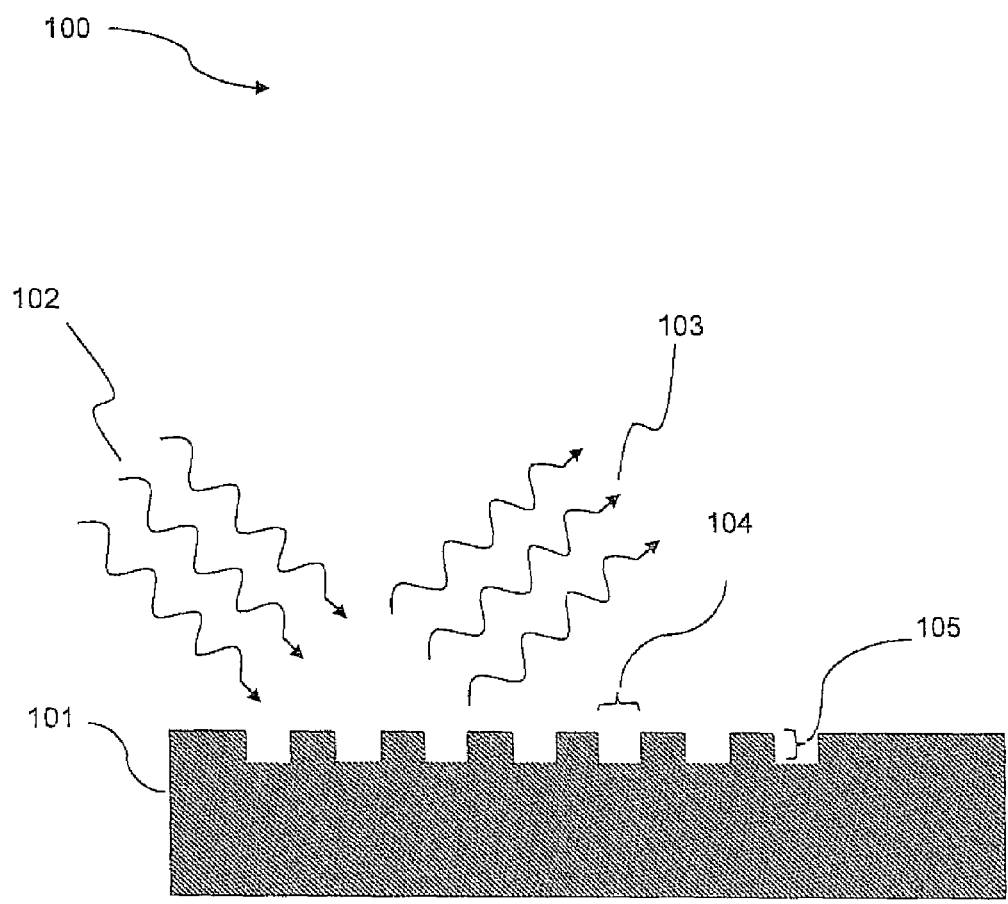
FIG. 1 is an exemplary illustration of micromachined substrate or wafer or coating showing reflection of light from a patterned surface with specific pore width and pore height.

The present invention provides a process and/or a sensor for fast detection of a pathogen such as *E-Coli*. As such, the present invention has use as a sensor.

The process includes providing a substrate and depositing a coating onto the substrate, the coating having an outer surface. During and/or after the coating is deposited onto the substrate, a textured outer surface is produced thereon, the textured outer surface having a plurality of hills and valleys such that a generally high surface area is produced with a nominal spacing between the plurality of hills and/or the plurality of valleys that minimizes internal scattering of a predetermined electromagnetic radiation wavelength and thus maximizes reflection of the predetermined electromagnetic radiation wavelength. In some instances, the coating can be a silicon coating and/or a biomarker substrate can be applied to the textured outer surface of the coating.

For example and for illustrative purposes only, a sensor manufactured according to the present invention can reflect at least 4000 relative luminescence units (RLUs) of electromagnetic radiation having a wavelength of approximately 530 nanometers after a solution containing an *E-Coli* concentration of $10^7$ colony-forming units per milliliter (CFU/ml) is placed onto the sensor for at least 60 seconds. In such an instance, a biomarker substrate containing dioxetane can result in an enzymatic reaction with the *E-Coli* such that electromagnetic radiation having a wavelength of approximately 530 nanometers is produced from the reaction.

In some instances, the sensor can reflect at least 5000 RLUs of electromagnetic radiation having a wavelength of approximately 530 nanometers after a solution containing an *E-Coli* concentration of $10^7$ CFU/ml is placed onto the sensor for at least 60 seconds, whereas in other instances the sensor reflects at least 6000 RLUs under the same conditions.

In the event that a solution containing an *E-Coli* concentration of $10^7$ CFU/ml is placed onto the sensor for at least 120 seconds, the sensor can reflect at least 6000 RLUs, at least 8000 RLUs in other instances, and/or at least 10000 RLUs. It is appreciated that such luminescence counts can be two times, three times, and/or four times greater than current state of the art sensors. As such, the process for manufacturing a sensor for fast detection of a pathogen according to the present invention provides an unexpected and dramatic increase in luminescence detection.

The coating can be deposited onto the substrate using a technique such as electrochemical deposition, laser ablation, thermal spray deposition, plasma deposition, physical vapor deposition, chemical vapor deposition, and/or combinations thereof. In addition, the textured outer surface can be produced by rapidly melting and quenching a plurality of discrete locations on the outer surface of the coating. The rapid melting and quenching of the plurality of discrete locations on the outer surface of the coating can be produced using a heat source such as a laser, an electron beam, a plasma, and the like.

Non-limiting embodiments will now be described more fully with reference to the accompanying drawings.

With particular reference to FIG. 1, for an incoming light 102 falling on a surface or wafer or coating 101 having a periodic patterned structure with specific pore width 104 and pore depth 105, the duly reflected light 103 represents the reflectance behavior of the patterned or textured structure 101.

Figure 2:
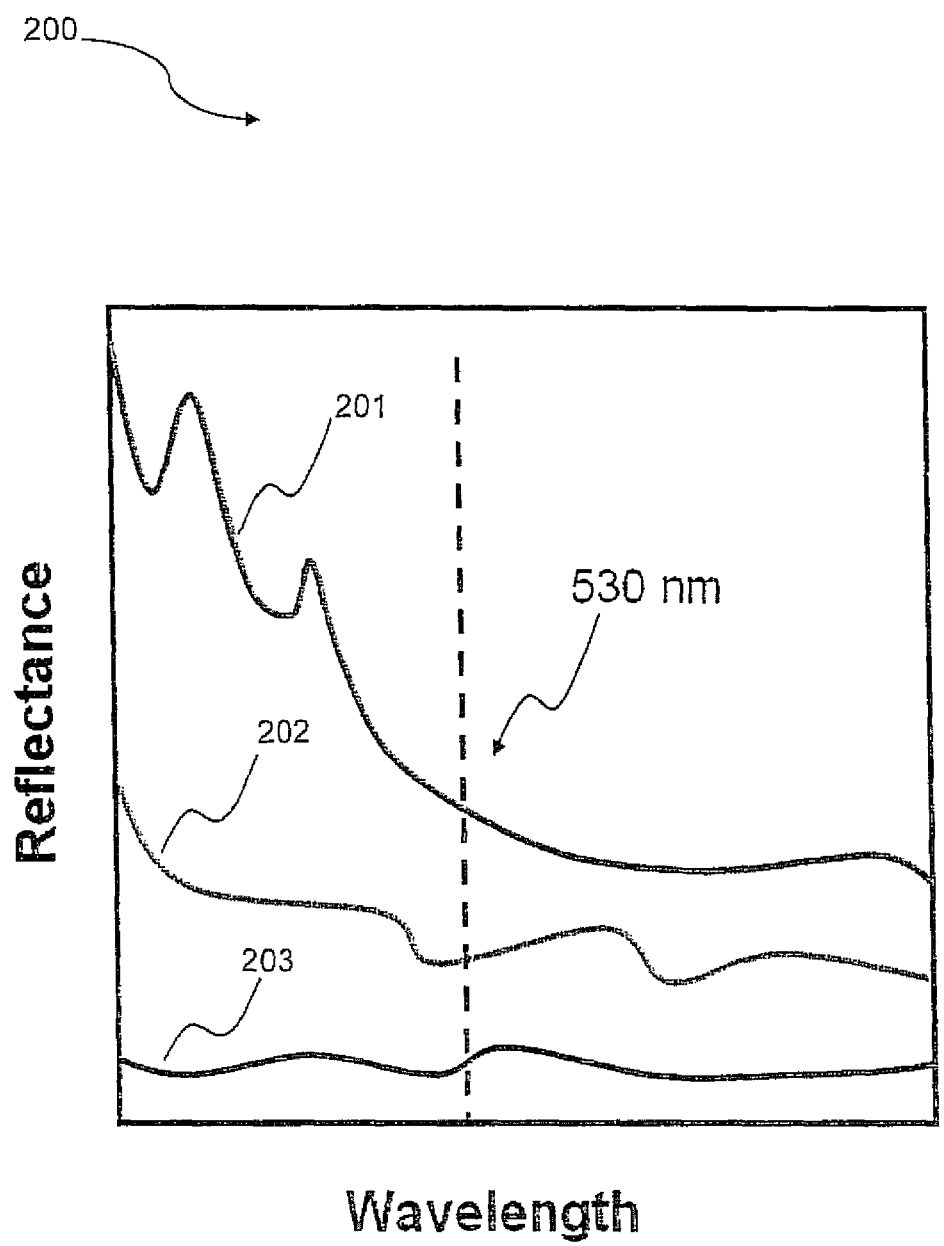
FIG. 2 is an exemplary illustration showing the reflectance from a micromachined substrate or wafer or coating with increasing pore depths in the visible spectrum.

As shown in FIG. 2, the reflectance behavior in the visible spectrum 201, 202 and 203 respectively, is considerably influenced by the pore depth 105 of the coating 101. As the pore depth 105 increases while keeping the pore width 104 constant, the reflectance is severely reduced due to internal scattering and absorption of the light within the pores. Compared to the reflectance of a flat surface 201, the reflectance from the patterned surfaces 202 and 203 reduces progressively with progressive increase in the pore depth 105.

According to the teachings of the present disclosure, an appropriate combination of pore width 104 and pore depth 105 can yield high reflectance from a textured or patterned surface while providing large surface area desired for fast chemiluminescence response. Furthermore, such desired patterned surface can be effectively processed by non-chemical etching processes according to the current teachings.

Figure 3:
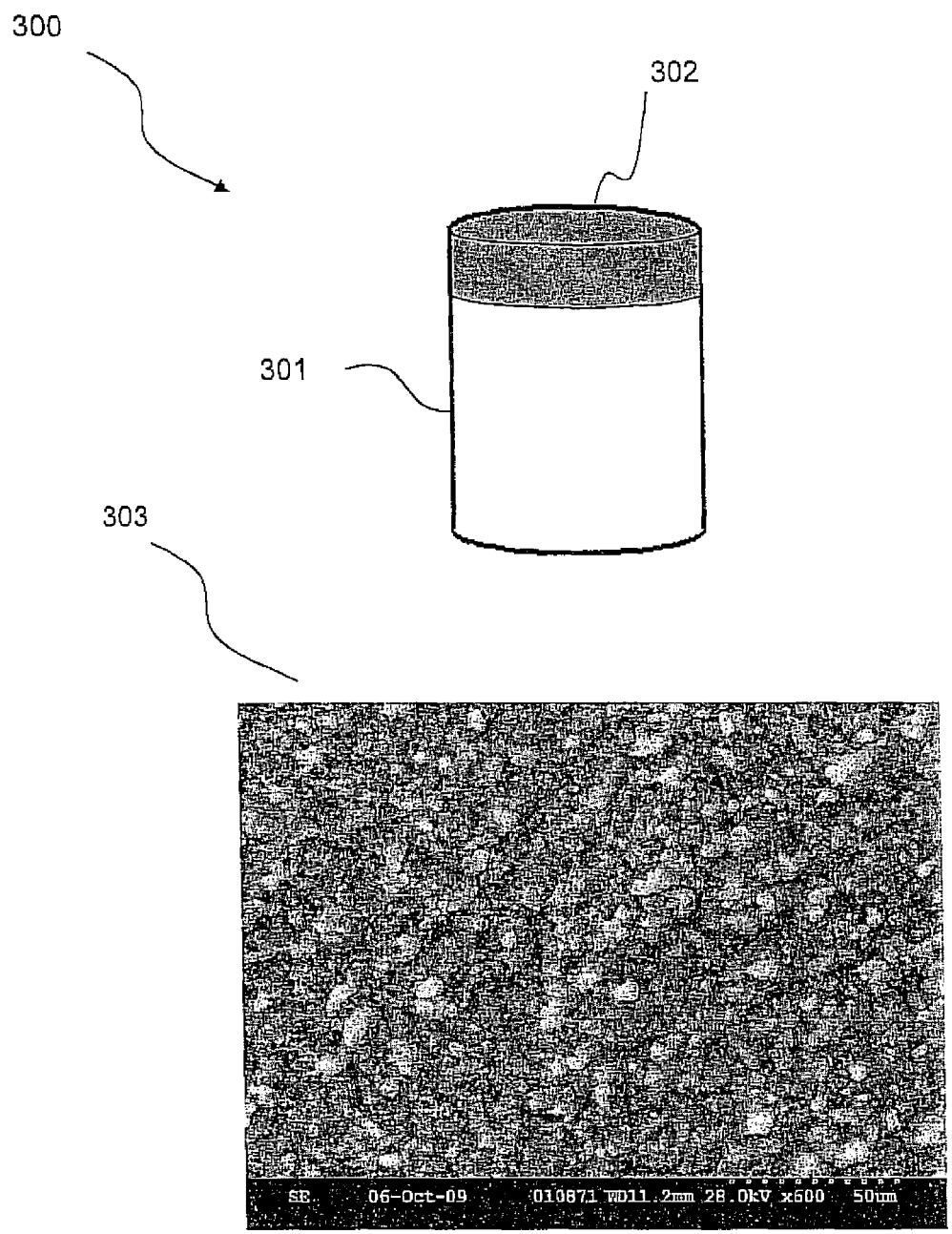
FIG. 3 shows an example of Si sensor prepared employing a DC plasma spray deposition and laser patterning technique, according to the teachings of this disclosure.

In some embodiments of the present teachings as shown in FIG. 3, a Si biochip 300 comprises a cylindrical substrate 301, a silicon coating 302 deposited employing plasma spray technique and silicon powder precursor, followed by a subsequent laser beam irradiation to develop the patterned surface with the desired attributes. 303 is an exemplary patterned Si structure viewed under a scanning electron microscope.

Figure 4:
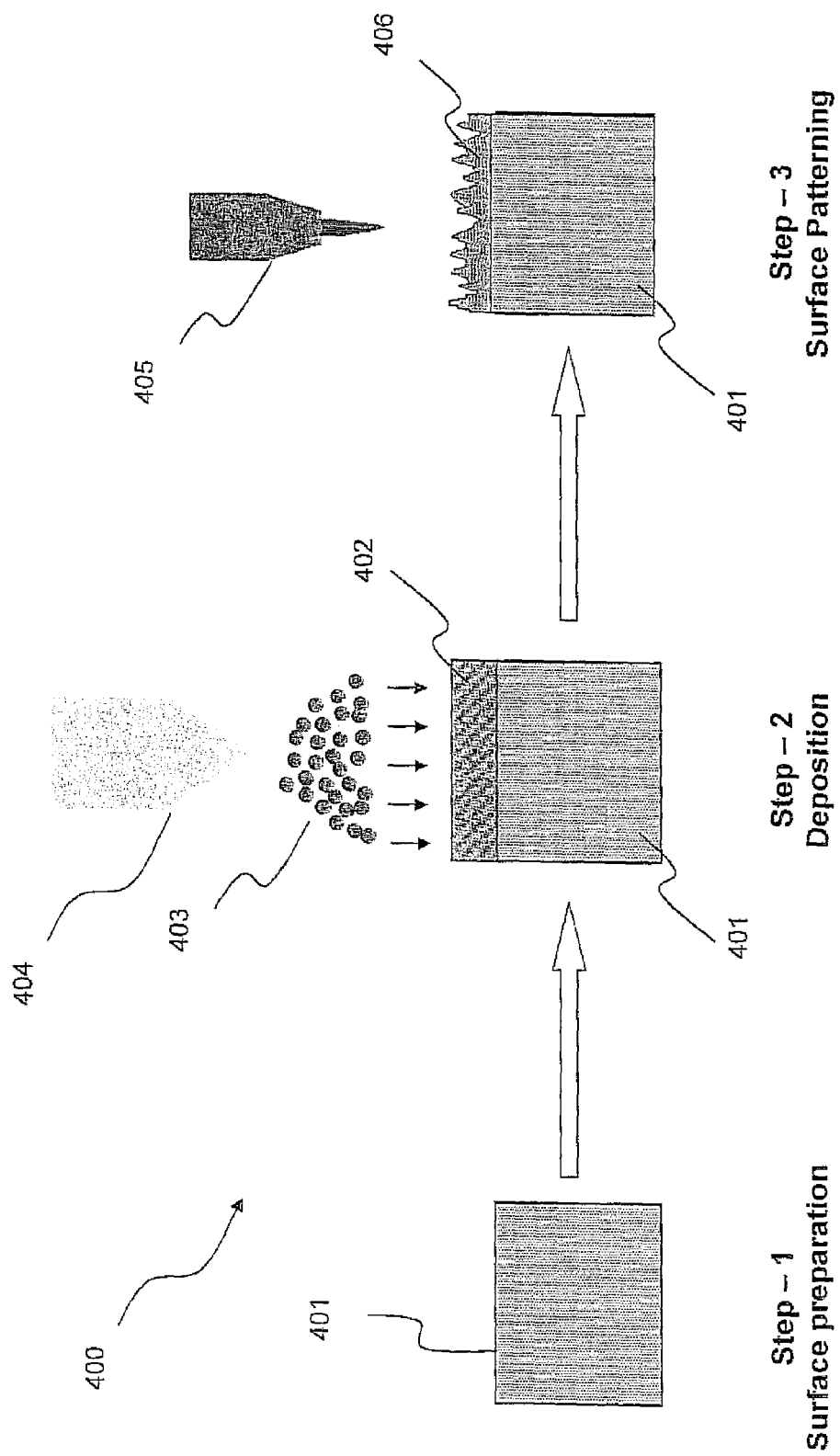
FIG. 4 is an exemplary illustration of a fabrication scheme for developing ultrafine/nanostructured sensor employing a deposition and patterning technique.

With particular reference to FIG. 4, the current teachings provide manufacturing schemes to fabricate the sensor using an appropriate precursor which is deposited by an additive process and simultaneously/subsequently treated by an energy beam to develop the desired textured surface. As schematically shown in FIG. 4, the manufacturing scheme comprises a surface preparation step, followed by a deposition step and finally a surface patterning step. The substrate 401 is used to deposit a precursor 403 to form a thin layer 402 employing an additive process 404. The thin layer 402 is subsequently textured 406, employing an energy beam 405.

According to the principles of the present teachings, the additive process 404 can be a vapor deposition or a spray deposition technique including, but not limited to, DC plasma, induction plasma, electron beam deposition, laser beam deposition, chemical vapor deposition (CVD) and plasma enhanced CVD (PECVD) technique. Similarly, the precursor material 403 can be a solid, or a liquid or a gas or their combination.

The surface patterning step 3 can be provided with a heat source 405 that is capable of treating the deposited material, layer by layer, nearly simultaneously as the layers are deposited by the additive process 404 on the substrate. The energy source can be a laser, plasma, electron, radiation or convection heat source. That is, the energy output from a heat source 405 can be directed to coating deposited on a substrate using the methods set forth herein. In this regard, each thinly-deposited layer on a substrate can be immediately modified, tailored, or otherwise processed by the heat source 405 in a simple and simultaneous manner. Specifically, the heat source 405 is disposed adjacent or integrally formed with additive device 404 to impart energy upon the substrate being processed. In some embodiments of the present teachings the energy beam can assume either a Gaussian energy distribution or rectangular energy distribution.

The surface patterning step involves fast melting of the surface layers of 402 following rapid quenching to develop patterned or textured surfaces 406 for enhanced reflectance and large surface area for sensor applications.

Figure 5:
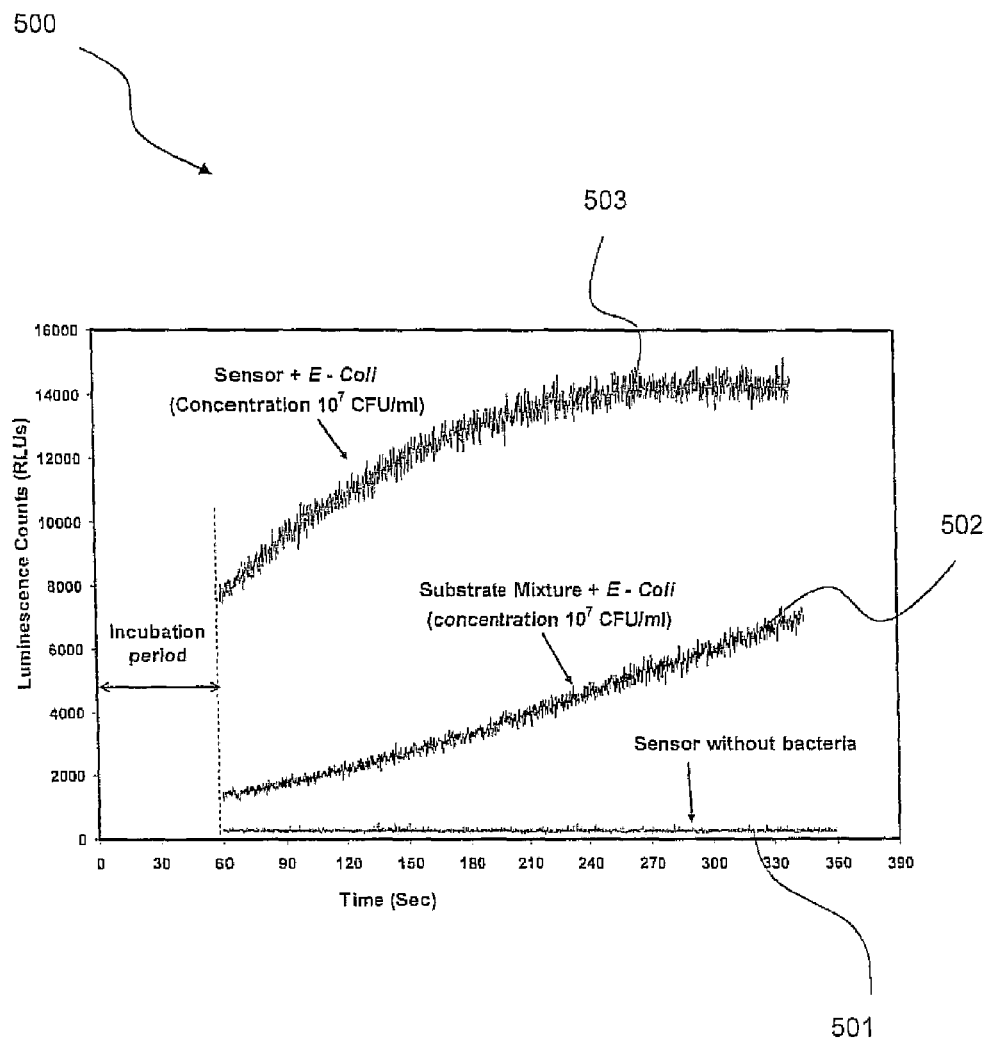
FIG. 5 shows an exemplary chemiluminescence response in the presence of *E-Coli* bacteria and biomarker substrate employing a sample of the Si sensor developed following the teachings of this disclosure.

FIG. 5 shows an exemplary application of the patterned Si structure 303 for sensing *E-Coli* bacteria following fictionalization process with the said "biomarker mixture" or "substrate mixture". The intensity or counts of emitted light photons (λ~530 nm) measured in relative light units as a function of time. Initial 60 seconds is an incubation period during which the photon counts are not measured. The Incubation period provides enough time for the *E-Coli* to release the β-Galactosidase enzyme and thus facilitate for the chemical reaction between the enzyme and biomarker substrate mixture either on the sensor surface or in the liquid state to start emit the light photons through chemiluminescence phenomenon. Curve 501 presents the luminescence counts from the functionalized sensor in the absence of *E-Coli*. Curve 502 presents the luminescence counts from the "Substrate Mixture and $10^7$ CFU/ml *E-Coli*" in the absence of the sensor. Curve 503 indicates the emitted photon intensity when the sensor and *E-Coli* interact inside the "Substrate Mixture" for a concentration of $10^7$ CFU/ml. The interaction between the "Substrate Mixture" and *E-Coli*, and the interaction between the "Sensor" and *E-Coli*, take place when the β-Galactosidase enzyme released by the *E-Coli* reacted with the "Substrate Mixture" and/or functionalized sensor surface. Based on these curves, the curve 502 emits lower photon intensity/counts compared to the curve 503 for a same concentration of *E-Coli* bacteria of $10^7$ CFU/ml. Thus enhanced efficiency of the sensor shows faster response and fast detection of *E-Coli* bacteria just after the incubation period compared to the only "Substrate Mixture".

The described methods, techniques, analogies, apparatus, measurements, data, designs, geometries, illustrations, components and the sensors are example only. The details presented are understood by those skilled as examples only. Therefore, the methods, apparatus and designs and sensors for monitoring and detecting the *E-Coli* have been described with reference to preferred embodiments. Also, the unforeseen or unanticipated changes or alternatives, modifications, improvements and variations of the current teachings therein may be subsequently appreciated or made by those skilled in the art without departing from the scope of the invention are also intended to be encompassed by the following claims.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises", "comprising", "including" and "having" are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on", "directly engaged to", "directly connected to" or "directly coupled to" another element or layer, there may be no intervening elements or layers present. Other words used to describe the relationship between elements should be interpreted in a like fashion (e.g., "between" versus "directly between", "adjacent" versus "directly adjacent", etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first", "second" and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner", "outer", "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

REFERENCES

1. Evangelyn C. Alocilja, Stephen M. Radke, "Market analysis of biosensors for food safety", Biosensors and Bioelectronics 18 (2003) 841-846.
2. Schaap, A. P., DeSilva, R., Akhavan, H., Handley, R. S., (1991)—"Chemical and enzymatic triggering of 1,2-dioxetanes: Structural effects on chemiluminescence efficiency". In: Stanley, P. E., Cricka, L. J. (Eds.), *Bioluminescence and Chemiluminescence Current Status*. Wiley, Chichester, pp. 103-106.
3. Finny P. Mathew, Evangelyn C. Alocilja, "Porous silicon-based biosensor for pathogen detection", Biosensors and Bioelectronics 20 (2005), pp. 1656-1661.
4. Beale, E. G., Deeb, B. A., Handley, R. S., Akhavan Tafti, H., Schaap, A. P., "A rapid and simple chemiluminescent assay for *Escherichia coli* beta-galactosidase", Biotechniques 12 (3) (1992), pp. 320-332.

The invention claimed is:

1. A sensor for detection of a pathogen comprising:
   a substrate;
   a coating attached to said substrate, said coating having a textured outer surface with a plurality of hills and valleys, said plurality of hills having a nominal spacing therebetween and operable to reflect a desired electromagnetic radiation wavelength, said textured outer surface having a rapidly melted and quenched microstructure, said plurality of hills having a peak height of 8 micrometers to 23 micrometers.

2. The sensor of claim 1, further comprising a biomarker adsorbed onto said textured outer surface of said coating.

3. The sensor of claim 2, wherein said biomarker is a chemiluminescence substrate.

4. The sensor of claim 3, wherein the chemiluminescence substrate contains dioxetane.

5. The sensor of claim 4, wherein said nominal spacing reflects an electromagnetic radiation wavelength of 530 nanometers.

6. The sensor of claim 5, wherein said textured outer surface reflects at least 4000 relative luminescence units (RLUs) of electromagnetic radiation having a wavelength of 530 nanometers after a solution containing an *E-Coli* concentration of $10^7$ colony-forming units per milliliter (CFU/ml) is placed onto said chemiluminescence substrate for at least 60 seconds.

7. The sensor of claim 6, wherein said textured outer surface reflects at least 5000 RLUs of electromagnetic radiation having a wavelength of 530 nanometers after a solution containing an *E-Coli* concentration of $10^7$ CFU/ml is placed onto said chemiluminescence substrate for at least 60 seconds.

8. The sensor of claim 7, wherein said textured outer surface reflects at least 6000 RLUs of electromagnetic radiation having a wavelength of 530 nanometers after a solution containing an *E-Coli* concentration of $10^7$ CFU/ml is placed onto said chemiluminescence substrate for at least 60 seconds.

9. The sensor of claim 5, wherein said textured outer surface reflects at least 6000 RLUs of electromagnetic radiation having a wavelength of 530 nanometers after a solution containing an *E-Coli* concentration of $10^7$ CFU/ml is placed onto said chemiluminescence substrate for at least 120 seconds.

10. The sensor of claim 5, wherein said textured outer surface reflects at least 8000 RLUs of electromagnetic radiation having a wavelength of 530 nanometers after a solution containing an *E-Coli* concentration of $10^7$ CFU/ml is placed onto said chemiluminescence substrate for at least 120 seconds.

\* \* \* \* \*